United States Patent

Bonse et al.

Patent Number: 5,998,418
Date of Patent: Dec. 7, 1999

[54] ENROFLOXACINE INJECTION OR INFUSION SOLUTIONS

[75] Inventors: Gerhard Bonse, Köln; Martin Hamm, Düsseldorf; Hanns-Peter Müller, Odenthal; Arundev Haribhai Naik, deceased, late of Monheim, by Neela Arundev Naik, heir; Martin Scheer, Wuppertal, all of Germany; Michael Stegemann, Kansas City, Mo.; Oliver Vetter, Burscheid, Germany

[73] Assignee: Bayer Aktiengesellschaft, Leverkusen, Germany

[21] Appl. No.: 08/875,061

[22] PCT Filed: Dec. 28, 1995

[86] PCT No.: PCT/EP95/05147

§ 371 Date: Jul. 7, 1997

§ 102(e) Date: Jul. 7, 1997

[87] PCT Pub. No.: WO96/21453

PCT Pub. Date: Jul. 18, 1996

[30] Foreign Application Priority Data

Jan. 13, 1995 [DE] Germany .............................. 195 00 784

[51] Int. Cl.⁶ .................................................. A61K 31/495
[52] U.S. Cl. ............................................................. 514/255
[58] Field of Search ................................................. 514/255

[56] References Cited

U.S. PATENT DOCUMENTS 4,670,444   6/1987   Grohe et al. ............................ 514/300

FOREIGN PATENT DOCUMENTS 82-302997   6/1982   European Pat. Off. .
3537761 A   4/1987   Germany .

*Primary Examiner*—Raymond Henley, III
*Attorney, Agent, or Firm*—Joseph C. Gil; Godfried R. Akorli

[57] ABSTRACT

The present invention relates to novel injection and infusion solutions of the following composition:

a) 0.1 to 20% by weight of enrofloxacin, based on the total weight of the solution, in the form of its salts with polyhydroxycarboxylic acids or amino acids or mixtures thereof, b) polyhydroxycarboxylic acids, amino acids or mixtures thereof in 0.1 to 5 molar excess, based on enrofloxacin;

c) optionally 0.1 to 30% by weight of formulation aids, based on the total weight of the solution;

d) water to 100% by weight.

4 Claims, No Drawings

ENROFLOXACINE INJECTION OR INFUSION SOLUTIONS

This application is a 371 PCT/EP95/05147 filed Dec. 28, 1995.

The present invention relates to novel injection or infusion solutions of enrofloxacin.

Solutions of quinolonecarboxylic acids for parenteral administration are already known from EP-OS (European Published Specification) 67 666. They are based on salts of the corresponding quinolonecarboxylic acids with various hydroxycarboxylic acids.

Injection or infusion solutions of quinolonecarboxylic acids, inter alia of ciprofloxacin, based on the lactic acid salts with an excess of acid, are known from EP-OS (European Published Specification) 138 018.

Aqueous infusion solutions of ca 0.01 to 0.5% of ciprofloxacin, to which acids are added for stabilization, are known from EP-OS (European Published Specification) 214 784. Lactic acid, in particular, is mentioned as the preferred acid in said document.

Injection solutions based on fine suspensions of quinolonecarboxylic acids are known from DE-OS (German Published Specification) 39 02 079.

The present invention relates to novel injection and infusion solutions of the following composition:

a) 0.1 to 20% by weight of enrofloxacin, based on the total weight of the solution, in the form of its salts with polyhydroxycarboxylic acids or amino acids or mixtures thereof;

b) polyhydroxycarboxylic acids, amino acids or mixtures thereof in 0.1 to 5 molar excess, based on enrofloxacin;

c) optionally 0.1 to 30% by weight of formulation aids, based on the total weight of the solution;

d) water to 100% by weight.

Compared with the injection solutions of enrofloxacin known hitherto, the solutions according to the invention have the advantage of a potent effect which sets in rapidly. This is shown by the fact that high blood levels of the active substance are reached only a short time after administration. However, the active substance is also eliminated rapidly, which is a great advantage, especially in the treatment of animals used for food production (short waiting times).

The injection and infusion solutions according to the invention contain the active substance enrofloxacin in concentrations preferably of 1 to 10%, particularly preferably of 2.5 to 10% (percent by weight based on the total weight of the solution).

Polyhydroxycarboxylic acids which may be mentioned are gluconic acid, galacturonic acid, glucuronic acid and lactobionic acid. The acids can be in the open-chain form or in the form of their lactones. If the acids are used as lactones, the lactone ring is at least partially hydrolyzed before salt formation and complex formation with enrofloxacin take place. Amino acids which may be mentioned are glutamic acid and aspartic acid. The polyhydroxycarboxylic acids or amino acids are present in 0.1 to 5 molar excess, based on the amount of enrofloxacin in the solution. The excess of acid is preferably 0.2 to 2 molar, particularly preferably 0.5 to 1 molar.

Part of the acid present in excess can also be displaced by other acids, e.g. hydrochloric acid, methanesulphonic acid, ethanesulphonic acid, propionic acid, succinic acid, glutaric acid, citric acid, ascorbic acid, phosphoric acid or lactic acid.

In addition to water for injections, the aqueous injection solutions can also contain ethanol, glycerol, propylene glycol, polyethylene glycol and triethylene glycol, for example, as liquid vehicles. The pH can be adjusted to the range 3 to 6.5, as far as possible, by using a variety of substances such as phosphoric acid, citric acid, Tris, ascorbic acid, acetic acid, succinic acid, tartaric acid, gluconic acid and lactic acid, and salts thereof. The pH of the aqueous formulations according to the invention is 3 to 5.5, preferably 3.5 to 5. The osmolality of the aqueous suspensions is 200 to 900 mOsmol/kg, preferably 260 to 390 mOsmol/kg, and can be adapted to isotonic conditions by the addition of NaCl, glucose, fructose, glycerol, sorbitol, mannitol, sucrose or xylitol, or mixtures of these substances.

It is further possible to use formulation aids such as thickeners (e.g. inter alia methyl cellulose, hydroxyethyl cellulose, hydroxypropyl cellulose, sodium carboxymethyl cellulose, polyvinylpyrrolidone and gelatin), absorbents, light stabilizers, crystallization retarders, complexing agents (e.g. inter alia NaEDTA, phosphates, nitrates, acetates and citrates), antioxidants (inter alia ascorbic acid, sulphite compounds, L-cysteine, thiodipropionic acid, thiolactic acid, monothioglycerol and propyl gallate) and preservatives (inter alia PHB esters, phenol and derivatives, chlorobutanol, benzyl alcohol, ethanol, butanol, butane-1,3-diol, chlorhexidine salts, benzoic acid and salts, and sorbic acid). Local anaesthetics, for instance procaine hydrochloride, lidocaine hydrochloride and the like, can optionally be added to the solutions according to the invention.

The injection or infusion solutions according to the invention can be prepared starting from the enrofloxacin salt with the corresponding acid or from a hydrate thereof.

It is also possible, however, to prepare the salts directly in the solution by adding the amounts of acid required for salt formation. The dissolution can be accelerated by working at temperatures of between 30 and 60° C. The solutions can be prepared under nitrogen gas.

In this way it is possible to prepare either ready-to-use solutions of the active substance filled into suitable containers, e.g. into ampoules, injection vials or infusion bottles, or precursors suitable for the preparation of such solutions, e.g. concentrates or lyophilized.

The containers into which the preparations are filled can be made either of glass or of plastic, it being possible for the container materials to include substances which give the contents a particular protection, e.g. Protection from light or oxygen.

The preparation of the solutions in the following Examples can be carried out in batch vessels with or without a heat transfer jacket. When using a non-heatable vessel, preheated water can be used if necessary.

In general, the bulk of the solvent is introduced into the vessel and the individual components are dissolved therein, although it is also possible to add the solvent to the solids.

When acids are used in the form of their lactones, they are hydrolyzed to the free acid after dissolution, generally by being heated or left to stand, before the active substance is added. The temperature used here is 40–70° C., preferably 50–60° C.

The other constituents are subsequently dissolved in or incorporated into the preparation before or after cooling, with stirring. After making-up with the remainder of the solvent, the formulation can be sterile-filtered through suitable bacteria-retaining filters and/or heat-sterilized.

EXAMPLES

Example 1

| | g/100 ml |
|---|---|
| Enrofloxacin 100% | 10.00 |
| Gluconolactone | 8.00 |
| Benzyl alcohol double dist. | 1.40 |
| Sodium sulphite | 0.10 |
| Water for injections | 86.70 |
| 100 ml = 106.20 | pH 3.90 |

Example 2

| | g/100 ml |
|---|---|
| Enrofloxacin 100% | 5.00 |
| Gluconolactone | 3.00 |
| Benzyl alcohol | 1.00 |
| Water for injections | 93.60 |
| 100 ml = 102.60 | pH 4.40 |

Example 3

| | g/100 ml |
|---|---|
| Enrofloxacin 100% | 5.00 |
| Glucuronic acid | 3.25 |
| Benzyl alcohol | 1.00 |
| Water for injections | 93.45 |
| 100 ml = 102.70 | pH 3.85 |

Example 4

| | g/100 ml |
|---|---|
| Enrofloxacin 100% | 5.00 |
| L-Glutamic acid puriss. | 2.50 |
| Benzyl alcohol | 1.00 |
| Water for injections | 93.80 |
| 100 ml = 102.30 | pH 5.15 |

Example 5

| | g/100 ml |
|---|---|
| Enrofloxacin 100% | 5.00 |
| Tartaric acid | 1.25 |
| Benzyl alcohol | 1.00 |
| Water for injections | 94.55 |
| 100 ml = 101.80 | pH 4.40 |

Example 6

| | g/100 ml |
|---|---|
| Enrofloxacin 100% | 10.000 |
| Gluconolactone | 4.000 |
| Acetic acid 100% | 1.175 |
| Benzyl alcohol | 1.400 |
| Sodium sulphite | 0.100 |
| Water for injections | 8.025 |
| 100 ml = 104.700 | pH 4.42 |

Example 7

| | g/100 ml |
|---|---|
| Enrofloxacin 100% | 10.000 |
| Gluconolactone | 4.000 |
| Glutamic acid | 2.670 |
| Benzyl alcohol | 1.400 |
| Sodium sulphite | 0.100 |
| Water for injections | 87.330 |
| 100 ml = 105.500 | pH 4.28 |

We claim:

1. An injectible or infusible solution comprising a salt formed from:

a) 0.1 to 20% by weight of enrofloxacin; and b) 0.1 to 5 molar excess, based on enrofloxacin, of gluconic acid, glucuronic acid, glutamic acid, tartaric acid or a mixture thereof;

and additionally comprising:

c) optionally 0.1 to 30% by weight of one or more formulation aids; and d) to 100% by weight of water; all amounts by weight being based on the total weight of the solution.

2. The injectible or infusible solution according to claim 1, wherein the amount of enrofloxacin is from 2.5 to 10% by weight of the solution.

3. A process for the preparation of an injectible or infusible solution according to claim 1 comprising stirring the enrofloxacin into an aqueous solution of acid or mixture of acids, optionally adding the formulation aids, and optionally diluting with additional water.

4. A method for combatting bacteria in an animal comprising injecting or infusing said animal with an injectible or infusible solution according to claim 1.

* * * * *